United States Patent [19]

Simard et al.

[11] Patent Number: 5,998,392
[45] Date of Patent: Dec. 7, 1999

[54] BENZOYL PEROXIDE FLOCCULENT MATERIALS AND METHODS OF THEIR PREPARATION

[75] Inventors: Veronique Simard, Lyons, France; David Garlen, Summit; Kenneth Klein, Fair Lawn, both of N.J.

[73] Assignee: Gattefosse s.a., Saint-Priest, France

[21] Appl. No.: 08/630,520

[22] Filed: Apr. 10, 1996

[51] Int. Cl.$^6$ .................................................. A61K 31/605
[52] U.S. Cl. ........................................ 514/164; 526/232.1
[58] Field of Search ........................... 514/164; 526/232.1

[56] References Cited

U.S. PATENT DOCUMENTS

| | | | |
|---|---|---|---|
| 4,606,913 | 8/1986 | Aronson et al. | 424/59 |
| 4,671,956 | 6/1987 | Bouillon et al | 424/59 |
| 5,019,567 | 5/1991 | Philippe et al. | 514/164 |
| 5,276,202 | 1/1994 | Ceh et al. | 568/559 |
| 5,460,620 | 10/1995 | Smith et al. | 604/290 |
| 5,562,642 | 10/1996 | Smith et al. | 604/290 |

*Primary Examiner*—Keith MacMillan
*Attorney, Agent, or Firm*—Brooks Haidt Haffner & Delahunty

[57] ABSTRACT

Improved compositions of benzoyl peroxide are prepared by at least partially dissolving benzoyl peroxide in diethylene glycol monoethyl ether to prepare a premixture which forms a flocculent composition of benzoyl peroxide when admixed with water or an aqueous medium. The improved benzoyl peroxide compositions have a small particle size compared with those prepared by conventional grinding techniques and the time and potential hazards associated with grinding are avoided. The small particle size of the benzoyl peroxide flocculents result in increased surface area of active ingredient on the skin for a given concentration of benzoyl peroxide. The flocculent compositions are used to prepare compositions for the topical treatment of acne or other dermatological disorders.

22 Claims, No Drawings

BENZOYL PEROXIDE FLOCCULENT MATERIALS AND METHODS OF THEIR PREPARATION

BACKGROUND OF THE INVENTION

1. Field of the Invention

The present invention has to do with improved compositions of benzoyl peroxide and methods of processing benzoyl peroxide. More particularly, the invention relates to the use of a composition such as TRANSCUTOL® diethylene glycol monoethyl ether as a processing aid for making a new benzoyl peroxide premixture which can be admixed with an aqueous medium to make a new benzoyl peroxide flocculent composition.

2. The Related Art

Benzoyl peroxide is most commonly employed as an active ingredient in topical compositions which are used in the treatment of acne and other dermatological conditions. Topically applied compositions used to treat the skin normally require that the benzoyl peroxide be ground to a fine particle size in a suitable vehicle before use. If the benzoyl peroxide is not ground, the product will be grainy and scratchy on the skin. Moreover, the clinical efficacy as related to the surface area of active ingredient on the skin, which in turn is a function of particle size, would be expected to be reduced for a given concentration of benzoyl peroxide when larger particles are employed. It is also known that benzoyl peroxide is a potentially explosive oxidizing agent and it must be ground under controlled conditions in a medium that prevents excessive heat build-up. Current manufacturing processes, therefore, are difficult, time consuming and potentially hazardous.

Benzoyl peroxide containing acne treatment compositions are disclosed in U.S. Pat. No. 4,606,913. The patent has to do with high internal phase emulsions and their use as suspending mediums for cosmetics and drugs. The emulsions are the water-in-oil type and, as an example, they can be used to make an acne cream comprised of water, mineral oil and benzoyl peroxide. The patent also discloses various cosmetic adjunct materials which can be used when the high internal phase emulsions are employed as a vehicle for cosmetic ingredients and these include solvents such as ethylene glycol monoethyl ether, diethylene glycol monoethyl ether, diethylene glycol monobutyl ether and several others. The compositions are prepared by adding the aqueous phase to the oil phase. Ingredients that are part of the aqueous phase are added into the aqueous phase before the phases are brought together.

Antiacne compositions combined with sun filters are disclosed in U.S. Pat. No. 4,671,956. The compositions are for the local treatment of acne and they contain from 0.5% to 20% by weight of benzoyl peroxide in association with at least one sun filter. The benzoyl peroxide is used in the form of a finely divided powder in the dry or moist state, preferably in the moist state. The antiacne compositions are in the form of emulsions and are prepared by adding benzoyl peroxide in the aqueous phase and the sun filter either in the aqueous phase or oil phase depending on its affinity. Propylene glycol is disclosed as an ingredient of the compositions as a humectant and solvents such as lower aliphatic alcohols can be incorporated in gel-type preparations.

According to U.S. Pat. No. 5,019,567, quaternary ammonium lipophilic salicylates are combined with benzoyl peroxide to prepare compositions for the treatment of dermatoses, acne, warts, skin dyskeratinization, cutaneous ulcers and other cutaneous disorders. The patent exemplifies gel compositions which include diethylene glycol monoethyl ether as an ingredient, among others, but there is no disclosure of the method of preparing the gel.

We have now discovered an improved method of processing benzoyl peroxide to make a premixture which can be admixed with an aqueous medium to make a new flocculent composition. The flocculent composition itself feels smooth or impalpable when rubbed on the skin. Our method is easier, faster and safer than conventional techniques which employ grinding to reduce the particle size of the benzoyl peroxide and the particles of benzoyl peroxide in our flocculent composition are substantially smaller than those which are obtained by conventional grinding.

SUMMARY OF THE INVENTION

A premixture of benzoyl peroxide is prepared by admixing benzoyl peroxide with diethylene glycol monoethyl ether, available from Gattefossé under the designation TRANSCUTOL®. The benzoyl peroxide is allowed to dissolve partially or completely in the TRANSCUTOL and the dissolution is preferably enhanced with agitation and/or heating above ambient temperatures. The premixture is then added to water to form a milky dispersion or flocculent having extremely small particles of benzoyl peroxide therein. Alternatively, the premixture can be added, blended, combined or otherwise mixed with an aqueous medium (i.e., a composition which contains water) which can be used in the preparation of a lotion, ointment, gel, cream, or the like.

Compositions of the invention are used in the treatment of acne and other dermatological disorders which are known to respond to treatment with benzoyl peroxide. The fine particle size of the benzoyl peroxide compositions of the invention is believed to improve the efficacy of the benzoyl peroxide because smaller particles provide increased surface area of active ingredient on the skin.

All percentages, parts and ratios expressed herein are by weight. The term admix as it is used herein is intended to encompass operations such as mixing, blending, combining and the like.

DETAILED DESCRIPTION OF THE INVENTION

The preferred benzoyl peroxide premixture composition of the invention is prepared by admixing benzoyl peroxide and TRANSCUTOL and partially or completely dissolving the benzoyl peroxide in the TRANSCUTOL. The ratio of benzoyl peroxide to TRANSCUTOL in the premixture can be from about 1:1 to about 1:18, preferably from about 1:2 to about 1:5 and most preferably from about 1:2 to about 1:4. While all of the benzoyl peroxide can be dissolved in the TRANSCUTOL, complete dissolving is not required in order to obtain acceptable results, namely, a composition which, when incorporated in a suitable topical composition, provides a smooth texture on the skin. The premixture accordingly can comprise an admixture wherein as much as 100% of the benzoyl peroxide is dissolved in TRANSCUTOL or as little as about 35% of the benzoyl peroxide is dissolved. More preferably, at least about 50% of the benzoyl peroxide should be dissolved and most preferably at about 100% should be dissolved.

Agitation of the admixture of benzoyl peroxide and TRANSCUTOL at ambient temperatures will shorten the time required for dissolution. Increasing the rate of agitation generally will increase the rate of dissolution. The temperature of the admixture also can be increased to enhance the rate of dissolution, and temperatures up to about 45° C. can be used. It is preferred, however, not to exceed temperatures of about 50° C. in order to avoid the violent decomposition of the benzoyl peroxide.

After the premixture is prepared it is used directly to prepare formulations for the topical application of benzoyl peroxide to the skin. Such formulations are prepared by admixing the premixture with water to make a flocculent before admixing the flocculent with other ingredients. Alternatively, the premixture can be admixed with an aqueous medium containing water and other ingredients, and this mixture becomes the aqueous phase of a water-in-oil or oil-in-water emulsion.

EXAMPLES

Example 1

Five parts of benzoyl peroxide were mixed with 10 parts of TRANSCUTOL diethylene glycol monoethyl ether to form a dispersion. Most of the benzoyl peroxide was dissolved. The dispersion was added to 85 parts of room temperature water and a milky dispersion (a flocculent composition) formed. When the milky dispersion was rubbed on the skin there was no grittiness and one could not feel the powder. Under microscopic examination, extremely small particles of benzoyl peroxide were observed.

For comparative purposes, 5 parts of benzoyl peroxide were mixed with 95 parts of water. When rubbed on the skin the particles were rough and scratchy. Under microscopic examination relatively large particles were observed, about ten times larger than the particles which had been admixed with TRANSCUTOL.

Example 2

The kinetics of dissolving benzoyl peroxide in TRANSCUTOL were studied. Five grams of benzoyl peroxide were admixed with 95 grams of TRANSCUTOL using a propellor mixer at about 500 rpm at room temperature of about 20° C. After 7 minutes, 90% of the benzoyl peroxide was dissolved and after 10 minutes 100% was dissolved.

What is claimed is:

1. A benzoyl peroxide composition consisting essentially of benzoyl peroxide and diethylene glycol monoethyl ether wherein at least about 35% of the benzoyl peroxide is dissolved.

2. The composition of claim 1 wherein at least about 50% of the benzoyl peroxide is dissolved.

3. The composition of claim 1 wherein the weight to weight ratio of benzoyl peroxide to diethylene glycol monoethyl ether is from about 1 to 1 to about 1 to 18.

4. The composition of claim 1 wherein the weight to weight ratio of benzoyl peroxide to diethylene glycol monoethyl ether is from about 1 to 2 to about 1 to 5.

5. The composition of claim 1 wherein the weight to weight ratio of benzoyl peroxide to diethylene glycol monoethyl ether is from about 1 to 2 to about 1 to 4.

6. A flocculent composition consisting essentially of benzoyl peroxide and diethylene glycol monoethyl ether wherein at least about 35 percent of the benzoyl peroxide is dissolved therein and an aqueous medium.

7. A method of reducing the explosive nature of a benzoyl peroxide composition comprising admixing benzoyl peroxide with diethylene glycol monoethyl ether and dissolving at least about 35% of the benzoyl peroxide therein.

8. The method of claim 7 wherein at least about 50% of the benzoyl peroxide is dissolved.

9. The method of claim 7 wherein about 100% of the benzoyl peroxide is dissolved.

10. The method of claim 7 wherein the weight to weight ratio of benzoyl peroxide to diethylene glycol monoethyl ether is from about 1 to 1 to about 1 to 18.

11. The method of claim 7 wherein the weight to weight ratio of benzoyl peroxide to diethylene glycol monoethyl ether is from about 1 to 2 to about 1 to 5.

12. The method of claim 7 wherein the weight to weight ratio of benzoyl peroxide to diethylene glycol monoethyl ether is from about 1 to 2 to about 1 to 4.

13. The method of claim 7 wherein admixing is by agitation.

14. The method of claim 7 further comprising heating up to a temperature of about 45° C. during admixing.

15. A method of reducing the explosive nature of a benzoyl peroxide flocculent composition comprising admixing diethylene glycol monoethyl ether with benzoyl peroxide, dissolving a portion of the benzoyl peroxide and then admixing with water or an aqueous medium.

16. The method of claim 15 wherein the weight to weight ratio of benzoyl peroxide to diethylene glycol monoethyl ether is from about 1 to 1 to about 1 to 18.

17. The method of claim 15 wherein the weight to weight ratio of benzoyl peroxide to diethylene glycol monoethyl ether is from about 1 to 2 to about 1 to 5.

18. The method of claim 15 wherein the weight to weight ratio of benzoyl peroxide to diethylene glycol monoethyl ether is from about 1 to 2 to about 1 to 4.

19. The method of claim 15 wherein admixing is by agitation.

20. The method of claim 15 further comprising heating up to a temperature of about 45° C. during admixing.

21. An aqueous composition for the topical treatment of acne or other dermatological disorders having as an active ingredient a benzoyl peroxide composition consisting essentially of benzoyl peroxide and diethylene glycol monoethyl ether wherein at least about 35% of the benzoyl peroxide is dissolved.

22. A lotion, ointment, gel or cream for the topical treatment of acne or other dermatological disorders having as an active ingredient a benzoyl peroxide composition consisting essentially of benzoyl peroxide and diethylene glycol monoethyl ether wherein at least about 35% of the benzoyl peroxide is dissolved.

* * * * *